United States Patent
Callegaro et al.

(10) Patent No.: US 8,771,672 B2
(45) Date of Patent: Jul. 8, 2014

(54) BIOLOGICAL MATERIAL SUITABLE FOR THE THERAPY OF OSTEOARTHROSIS, LIGAMENT DAMAGE AND FOR THE TREATMENT OF JOINT DISORDERS

(75) Inventors: Lanfranco Callegaro, Abano Terme (IT); Anna Maria Zanellato, Albano Terme (IT)

(73) Assignee: Fidia Farmaceutici S.p.A., Abano Terme (IT)

( * ) Notice: Subject to any disclaimer, the term of this patent is extended or adjusted under 35 U.S.C. 154(b) by 0 days.

(21) Appl. No.: 13/380,971

(22) PCT Filed: Jun. 29, 2010

(86) PCT No.: PCT/EP2010/059183
§ 371 (c)(1),
(2), (4) Date: Jan. 4, 2012

(87) PCT Pub. No.: WO2011/000820
PCT Pub. Date: Jan. 6, 2011

(65) Prior Publication Data
US 2012/0114609 A1 May 10, 2012

(30) Foreign Application Priority Data

Jul. 2, 2009 (IT) ............... MI2009A1171

(51) Int. Cl.
*A61K 35/12* (2006.01)
*A61K 35/16* (2006.01)
*A61P 17/02* (2006.01)
*A61P 19/00* (2006.01)
*A61P 19/02* (2006.01)

(52) U.S. Cl.
USPC ............ 424/93.3; 424/93.7; 424/93.72

(58) Field of Classification Search
CPC . A61L 27/3616; A61L 27/3834; A61L 27/20; A61L 27/60; A61K 35/19; A61K 35/28; A61K 9/0024; A61K 47/36; A61K 9/06; A61K 47/38; A61K 9/0014; A61K 35/16
See application file for complete search history.

(56) References Cited

U.S. PATENT DOCUMENTS

| 6,884,428 B2 * | 4/2005 | Binette et al. ............ 424/422 |
| 8,034,014 B2 * | 10/2011 | Higgins et al. ............ 604/4.01 |
| 2009/0274627 A1 * | 11/2009 | Yamada et al. ............ 424/9.2 |

FOREIGN PATENT DOCUMENTS

| WO | WO-2009/016451 A2 | 2/2009 |
| WO | WO-01/80865 A2 | 11/2011 |

OTHER PUBLICATIONS

Okabe et al., May 2009; Injectable soft-tissue augmentation by tissue engineering and regenerative medicine with human mesenchymal stromal cells, platelet-rich plasma and hyaluronic acid scaffolds, Cytotherapy vol. 11, No. 3, 307-316.*
Anitua, Eduardo et al., "New insights into and novel applications for platelet-rich fibrin therapies," Trends in Biotechnology, May 1, 2006, vol. 24, No. 5, pp. 227-234.
Borzacchiello, A. et al., "Effect of hyaluronic acid amide derivative on equine synovial fluid viscoelasticity," Journal of Biomedical Materials Research, Mar. 25, 2009, vol. 92A, No. 3, pp. 1162-1170.

* cited by examiner

*Primary Examiner* — Karen Cochrane Carlson
*Assistant Examiner* — Jennifer M. H. Tichy
(74) *Attorney, Agent, or Firm* — Birch, Stewart, Kolasch & Birch, LLP

(57) ABSTRACT

The present invention regards a biological material comprising: a) a liquid carrier comprising a viscous solution containing at least one natural and/or semisynthetic polysaccharide, and having a Dynamic viscosity measured at 20° C. and at shear rate of $D=350\ s^{-1}$, comprised between 100 and 250 c Poise and/or a Kinematic viscosity comprised between 99 and 248 cSt (measured at the same conditions); b) a culture of mesenchymal stem cells, and/or c) a platelet-rich hemo-derivative. This type of material in form of viscous liquid is particularly suitable for the therapy of osteoarthrosis, ligament damage, in particular tendon and cartilage damage) and may be administered intra-articularly, intradermally or directly applied in situ without altering the properties of the mesenchymal stem cells and/or platelets contained therein.

15 Claims, No Drawings

BIOLOGICAL MATERIAL SUITABLE FOR THE THERAPY OF OSTEOARTHROSIS, LIGAMENT DAMAGE AND FOR THE TREATMENT OF JOINT DISORDERS

This application is the National Phase Under 35 U.S.C. §371 of PCT International Application No. PCT/EP2010/059183 which has an International filing date of Jun. 29, 2010, which claims priority to Italian Patent Application No. MI2009A 001171 filed on Jul. 2, 2009. The entire contents of all applications listed above are hereby incorporated by reference.

FIELD OF THE INVENTION

The present invention regards a biological material in viscous liquid form suitable for the therapy of osteoarthrosis, tendons, ligaments damage, for the treatment of joint and connective tissues disorders in general, and damaged skin.

PRIOR ART

The joint cartilage is particularly suitable to resist against compression, it neither has blood supply nor lymphatic drainage and it is entirely free of nerve endings. This implies that it is not capable of self-regeneration to compensate a surface lesion, unless the underlying subchondral layer is not involved.

Thus, if the cartilage lesion is not deep, there will be no regenerative response. On the contrary, if the damage is deep and penetrates into the subchondral bone, it triggers a self-reparative process hence the bone marrow stem cells start a chondrocyte differentiation process which may lead to partial reparation of the damaged cartilage.

Symptoms, such as pain and swelling of the joint (such as for example the knee), may be the result of a damaged cartilage and the progressive degeneration of the same may develop osteoarthritis.

This type of lesion may frequently occur in professional athletes (in that they are more subjected to trauma), or in elderly patients, due to joint trauma and postural defects, or to the normal wear of the cartilage related to the age of the subject.

Actually, in the chondral lesions of the knee joint, non-surgical treatments of this type which include physiotherapy and medication, do not allow complete healing of the cartilage defect which instead was attained, with good percentages of success, after the performance of particularly innovative intra-articular surgical implantation operations.

The main surgical cartilage repair techniques known in the prior art are:

1. autologous chondrocyte implantation through at least two different surgical procedures in sequence: the first, less invasive, provides for the collection (by means of arthroscopy) of a normal cartilage tissue of the patient from other non-injured areas of the joint, or from a non-articular cartilage. The collected sample is thus sent to a laboratory for in vitro cellular expansion. Once the chondrocytes multiply, there follows the actual surgical operation consisting in grafting, directly in the lesion site, the produced chondrocytes (vehicled in saline solutions) which may be possibly "fixed in situ" with autologous periosteal tissue. This process is extremely expensive in that it requires 2 surgical operations and the process for in vitro growth of the chondrocytes. Thus, this entails the double admission of the patient in hospital, hence the patient being subjected twice to anaesthesia and twice to pharmacological treatment.

2. A second simpler method consists in performing perforations on the joint surface to reach the subchondral tissue of the injured area and thus allow the formation of a mesenchymal blood clot capable of reaching the cartilage defect surface, where the cells may partly differentiate into chondrocytes. However, the newly formed cartilage tissue was mainly fibrous and non-hyaline like the initial cartilage and, thus, it shall not have the same physical and mechanical characteristics of the native joint.

3. Known for the treatment of osteocartilaginous lesions, is the insertion of surgical implantations or polymer scaffolds containing chondrocytes and/or mesenchymal stem cells. In this case, the material which constitutes the scaffold may be semisynthetic polysaccharide such as, for example, a derivative of the hyaluronic acid[1], or consist in collagen matrices. Even this procedure was particularly expensive and required double admission of patient in hospital and a double operation, as described previously.

Another very common type of lesion and/or inflammation of the connective tissues is the lesion of ligaments or tendons, and in particular that of the Achilles tendon, especially among professional athletes, generally treated (in its most serious forms) even surgically due to the need of partial or total reconstruction of the injured tissue. Up to date, the surgical techniques used to repair ligaments were based on the graft of tissues and on synthetic prostheses, which however have a limited efficiency over time. Recent scientific publications have instead proven the capacity of the stem cells to reconstruct the tissue of the damaged tendons and ligaments: mesenchymal cells collected from the same stem cells introduced into the injured Achilles tendon, were in fact transformed into tenocytes (typical cells of the tendon). The tendon was thus repaired due to an increase of production of collagen which makes the ligaments flexible and resistant.

Recently, both in maxillofacial and bone surgery[2] but also (and above all) in the connective tissues surgery (and particular in the reconstruction/regeneration of tendons/ligaments and skin), the use of platelet-rich hemo-derivatives has become more and more common, in that this type of material is rich in trophic factors such as AGF (Autologous growth factor concentrate), and in particular PDGF-AB and TGFβ etc[3],[4].

These hemo-derivatives are in fact used for stimulating the reparative processes of the damaged skin following to the presence of venous ulcers, mainly in diabetic patients.

The stimulation is normally triggered with different methodologies, as for example:

a) mechanical stimulation,
b) local application of growth factors,
c) local application of tissue engineering products.

The mechanical stimulation consists in the abrasion of the bottom and edges of the lesion with a dry sterile gauze or with a bistoury up to bleeding. The local application of growth factor with a platelet concentrate dissolved in plasma allows the release of PDGF (with mitogen and angiogenetic action), TGF-B (for fibroblasts stimulation) EGF (for epidermal and mesenchymal cells stimulation) and IGF (as promoter of cellular duplication). The experimentation has demonstrated an increase in tissue vascularization although these hemo-derivatives are difficult to be handled and their permanence in situ has a very short duration.

The tissue engineering products are more recent and are in the form of heterologous fibroblasts and keratinocytes on a biocompatible support or in the form of autologous fibroblasts on a hyaluronic acid support.

This entails the use of surgical practice to take the cells from the patient in order to grow them in vitro before loading them on the support.

Considering the previously described state of the art, both regarding the intra-articular or intradermal administration of the cellular component and the treatment—with platelet products—of the injured regions of tendons/ligaments or skin (both cellular components and platelet rich hemo-derivative being administered by means of special syringes), there arises the need of providing a "carrier" that is sufficiently fluid but also capable of simultaneously ensuring:

a good physical/mechanical consistency, to allow the abovementioned administration safeguarding the vitality, the morphology of the cellular membranes and, simultaneously, the capacity of proliferation and differentiation of the vehicled cells, but which, in addition, allows maintaining the abovementioned cells in the lesion site without requiring further fixing needing subsequent suturing and medications.

Due to similar reasons, it is necessary to provide a "carrier" capable of safeguarding the integrity of the platelet hemo-derivatives to be used, in order to guarantee all biochemical and enzymatic properties of the proteins (i.e. the abovementioned trophic factors) contained therein and which, above all, allows maintaining administered active ingredients in the lesion site.

SUMMARY OF THE INVENTION

Now, the applicant has discovered that it is possible to overcome the abovementioned drawbacks of the prior art by means of the biological material according to the present invention.

In particular, the biological material according to the present invention comprises:

a) a liquid carrier comprising a viscous solution containing at least one natural and/or semisynthetic polysaccharide, and having a Dynamic viscosity measured at 20° C. and at shear rate of $D=350\ s^{-1}$, comprised between 100 and 250 cPoise and/or a Kinematic viscosity comprised between 99 and 248 cSt (measured at the same conditions);

b) a culture or an extemporaneous preparation of mesenchymal stem cells, and/or c) a platelet-rich hemo-derivative.

This type of material is suitable for the therapy of osteoarthrosis, cartilage damage, tendon damage (in particular the Achilles tendon damage), ligaments and, generally, in the joints and connective tissues disorders in general and damaged skin.

In addition, the present invention further relates to pharmaceutical compositions comprising the biological material of the present invention, in particular suitable for intra-articular, intradermal administration, but also for direct application in the lesion site.

DETAILED DESCRIPTION OF THE INVENTION

Relating to the present invention, the term viscous solution is used herein to indicate a homogeneous mixture of two or more components present in which is a solute i.e. the natural and/or semisynthetic polysaccharide entirely dissolved in a solvent usually water, where the term "water" is used to indicate water for injectable preparations, saline solution, etc.

This type of solution should not be confused with the so-called gel or hydrogel i.e. a semisolid product, whose components do not dissolve in the solvent, but remain suspended therein and it is generally made of material which is obtained through the creation of three-dimensional bonds (the so-called crosslinking) of the covalent chemical type, a hydrogen bond or Van der Waals bond between the various components of the gel and/or solvent.

The carrier in liquid form (a) in the biological material according to the present invention is preferably the viscous solution containing the natural and/or semisynthetic polysaccharide.

According to an even more preferred embodiment of the present invention, the carrier (a) in liquid form is the viscous solution essentially consisting of a polysaccharide of natural and/or semisynthetic origin and water.

Regarding the present invention, the expression "essentially consisting of" is used to indicate that a possible third component is present in concentrations comprised between 0.9 and 0.001% on the total weight of the viscous solution.

The polysaccharide of natural origin is preferably selected from hyaluronic acid (HA), cellulose, gellan, chitin, chitosan, pectine or peptic acid, agarose, alginic acid, alginates, starch, polymannans, polyglycans, whose molecular weight as well as the type of the molecule, is such as to allow/guarantee the formation of a viscous solution (and not a gel) having a Dynamic or Kinematic viscosity comprised in the abovementioned ranges.

The polysaccharide of semisynthetic origin is preferably selected from hyaluronic acid derivatives already known to the man skilled in the art such as, for example, the benzyl esters of hyaluronic acid described in EP 216453, its octyl, octadecyl, dodecyl and hexadecyl amide (EP1095064), and cellulose esters, such as carboxymethylcellulose (CMC) and collagen derivatives. In any case, these natural and semisynthetic polysaccharides must have a molecular weight such that the viscosity thereof is comprised in the abovementioned ranges, in addition they must exhibit molecular/physical chemical characteristics leading to the formation of a viscous solution and not a gel.

Only this type of viscosity allows obtaining a formulation suitable to be injected intra-articularly or in the lesion sites of tendons and/or ligaments, intradermally administered in case of cutaneous lesions, capable both of ensuring the highest vitality of the cells therein contained, as well as maintaining integer all the biochemical and enzymatic properties of the trophic factors contained in the platelet-rich hemo-derivatives, possibly present.

Used according to a particularly preferred form of realization of the invention, are:

a hyaluronic acid or a pharmaceutically acceptable salt thereof, preferably sodium salt, with average molecular weight comprised between 450 and 730 kDa (medium molecular weight (MW) HA); the concentration shall be comprised between 5 and 15 mg/ml, more preferably 10 mg/ml.

a hyaluronic acid or a pharmaceutically acceptable salt thereof, preferably sodium salt, with average molecular weight comprised between 1000 and 1800 KDa measured after sterilisation (high molecular weight (MW) HA); the concentration shall be comprised between 2 and 12 mg/ml, more preferably between 6 and 8 mg/ml.

The octylamide of hyaluronic acid, preferably with medium molecular weight (MW), therefore a hyaluronic acid having an average molecular weight comprised in the aforesaid range between 450 and 730 kDa; the concentration of this amide shall be comprised between 1 and 10 mg/ml, more preferably between 2 and 3 mg/ml.

The hexadecylamide of hyaluronic acid, preferably with medium molecular weight (MW) therefore a hyaluronic acid having an average molecular weight comprised in the aforesaid range between 450 and 730 kDa; the concentration of this amide shall be comprised between 0.2 and 1.5 mg/ml, more preferably between 0.5 and 1 mg/ml.

Gellan; the concentration shall be comprised between 2 and 8 mg/ml, more preferably 4 mg/ml.

CMC; the concentration shall be comprised between 15 and 40 mg/ml, more preferably 25 mg/ml.

Mesenchymal stem cells may be of the autologous and heterologous type and they are preferably those coming from the bone marrow, peripheral blood, periosteum, umbilical cord or adipose tissue.

For the scope of the present invention, the expression platelet-rich hemo-derivatives is used to indicate all platelet-rich hemo-derivatives, for example, platelet-rich plasma (PRP), i.e. the supernatant liquid coming from the centrifugation of the venous blood, the platelet concentrate (PC), i.e. the heavier liquid phase coming from the centrifugation of the platelet-rich plasma, and lastly the platelet gel, i.e. the platelet concentrate which due to the action of the precipitation agents (such as for example thrombin)—is transformed into gel[5].

Depending on the intended use and the type of lesion, it is possible to select the type of platelet-rich hemo-derivative. As a matter of fact, the three products are rich in the abovementioned trophic factors.

The biological material according to the present invention contains components (a) and (b) or (a) and (c), or the three components (a), (b) and (c).

Furthermore, it is preferable to add the autologous component (c) to the biological material comprising (a) and (b): the abovementioned platelet-rich hemo-derivative comes from the same patient and this product may even be prepared shortly before the patient is subjected to the abovementioned intra-articular injection or intradermal administration, or before the abovementioned material is applied directly onto the lesion site.

The pharmaceutical compositions according to the present invention can therefore be used in orthopedy in the (mainly extemporaneous) treatment of cartilage and bone defects (including local use in odontoiatry to favour the plants grip) and can be directly injected in the lesion site of damaged tendons and/or ligaments or can be used in dermatology both as injectable compositions for an intradermal administration or for topical use for the local treatment of cutaneous ulcers/lesions difficult to heal/recover.

Example 1

Preparation of a Viscous Solution Containing Medium Molecular Weight HA $1^{st}$ stage: hydration An amount of the HA sodium salt polysaccharide (500-730 KDa MW) equal to 100 mg is weighed to prepare a viscous solution with a final concentration of 10 mg/ml. The powders are hydrated with 50% of the required final volume (5 ml) using a 0.9% saline solution of Sodium chloride, phosphate buffer or water for injectable preparations, to obtain the desired final concentration.

$2^{nd}$ stage: solubilisation

The product obtained as described in stage 1, is subjected to magnetic stirring at ambient temperature for at least 1 hr.

The remaining volume (5 ml) is subsequently added to reach the established final concentration, and left under stirring for at least 2 hrs up to complete dissolution of the powders.

The solution thus obtained is subjected to sterilisation by means of an autoclave or UV radiation and, thus, subjected to the measurement of the Dynamic viscosity by means of a HAAKE RS150 Rheometer, at 20° C., at shear rate of D=350 $s^{-1}$.

The Dynamic viscosity obtained was of 155 cP, thus the product shall have a Kinematic viscosity of 153.6 cSt.

Example 2

Preparation of a Viscous Solution Containing High Molecular Weight HA

The process is performed like in example 1 starting from high molecular weight powders of HA to prepare two viscous solutions with a final concentration of 6 mg/ml and 8 mg/ml in WFI grade water.

The obtained solutions are sterilised and thus subjected to the measurement of the Dynamic viscosity by means of HAAKE RS150 Rheometer, at 20° C., at shear rate of D=350 $s^{-1}$.

The Dynamic viscosities obtained were respectively: 158 cP and 246 cP.

Example 3

Preparation of a Viscous Solution Containing Gellan

The process is performed like in example 1 starting from the powders of gellan to prepare a viscous solution with a final concentration of 4 mg/ml in saline solution.

The solution thus obtained is sterilised and then subjected to the measurement of the Dynamic viscosity by means of a HAAKE RS150 Rheometer, at 20° C., at shear rate of D=350 $s^{-1}$ The Dynamic viscosity obtained was of 110 cP, Example 4

Preparation of a Viscous Solution Containing CMC

The process is performed like in example 1 starting from the powders of CMC to prepare a viscous solution with a final concentration of 25 mg/ml in phosphate buffer.

The solution thus obtained is sterilised and then subjected to the measurement of the Dynamic viscosity by means of a HAAKE RS150 Rheometer, at 20° C., at shear rate of D=350 $s^{-1}$ The Dynamic viscosity obtained was of 220 cP, Example 5

Preparation of a Viscous Solution Containing the Octylamide or the Hexadecylamide of HA with Medium Molecular Weight (MW)

The process is performed like in example 1 starting from the powders of the octylamide (or from the hexadecylamide) of medium molecular weight HA, to prepare two viscous solutions with a final concentration of 2 mg/ml and 3 mg/ml, (or of 0.5 mg/ml and 1 mg/ml for the hexadecylamide) in saline solution of sodium chloride 0.9%.

The solutions thus obtained (after sterilisation) are subjected to the measurement of Dynamic viscosity by means of a HAAKE RS150 Rheometer, at 20° C., at shear rate of D=350 $s^{-1}$.

The Dynamic viscosities obtained were respectively: 143 cP and 220 cP for the octylamide, and 160 cP and 230 cP for the hexadecylamide of HA.

CITED BIBLIOGRAPHY (1)EP 0863776;
(2)"Fattori di crescita autologhi nella chirurgia ossea ricostruttiva dopo infezione" Carlo R. Romanòn et al, Unità operativa Chirurgia delle Complicanze Osteoarticolari Settiche (C.O.S., Istituto Ortopedico Gaetano Pini).
(3)"Different preparation methods to obtain components as a source of growth factors for local applications" R. Zimmermann et al., Transfusion 2001; 41:1217-1224.
(4)"Platelet-rich plasma preparation using three devices: Implications for platelet growth factor release" P. A. M. Everts et al., Growth Factors, September 2006; 24(3):165-171.
(5)U.S. Pat. No. 6,841,170

The invention claimed is:

1. A therapeutic method for the treatment of at least one member selected from the group consisting of osteoarthrosis, cartilagineous defects, bone defects, damaged tendon, damaged ligament, joint disorders, skin lesion and skin ulcers comprising injecting into a subject in need thereof a biological material comprising:
   component (a): a liquid carrier comprising a viscous solution containing at least one member selected from the group consisting of natural polysaccharides and semi-synthetic polysaccharides, and having a dynamic viscosity of and between 0.1 and 0.25 Pa·s (100 and 250 cPoise) measured at 20° C. at shear rate of D=350 s$^{-1}$, and/or a Kinematic viscosity comprised between 0.99× 10$^{-4}$ and 2.48×10$^{-4}$ m$^2$/sec (99 and 248 cSt) measured at 20° C. and at shear rate of D=350 s$^{-1}$, and
   component (b): at least one member selected from the group consisting of (i) a culture or an extemporaneous preparation of mesenchymal stem cells, and (ii) a platelet rich hemo-derivative;
   wherein said viscous solution of the component (a) is selected from the group consisting of:
   (I). an aqueous solution of a hyaluronic acid or a pharmaceutically acceptable salt thereof, with average molecular weight of between 450 and 730 kDa in a concentration of 10 mg/ml, and
   (I). an aqueous solution of hexadecylamide of hyaluronic acid having an average molecular weight in the range of 450 and 730 kDa, in a concentration of between 0.2 and 1.5 mg/ml.

2. The therapeutic method according to claim 1, wherein said viscous solution of component (a) is the aqueous solution (II), and the concentration of said hexadecylammide of hyaluronic acid in said aqueous solution is between 0.5 and 1 mg/ml.

3. The therapeutic method according to claim 1, wherein said component (b) comprises mesenchymal stem cells of the autologous type selected from the group consisting of: bone marrow mesenchymal stem cells, peripheral blood mesenchymal stem cells, periosteum mesenchymal stem cells, umbilical cord mesenchymal stem and cells of adipose tissue.

4. The therapeutic method according to claim 1, wherein said component (b) comprises platelet-rich hemo-derivatives selected from the group consisting of platelet-rich plasma, platelet concentrate, and platelet gel.

5. The therapeutic method according to claim 1, wherein said component (b) comprises (i) and (ii).

6. The therapeutic method according to claim 1, wherein said treatment is for the treatment of Achilles tendon damage.

7. The therapeutic method according to claim 1, wherein said aqueous solution (I) comprises sodium salt of hyaluronic acid.

8. The therapeutic method according to claim 1 for the treatment of cartilage damage comprising intra-articularly injecting said biologic material.

9. The therapeutic method according to claim 1 for the treatment of skin lesions and ulcers comprising intra-dermally injecting said biological material.

10. A therapeutic method for the treatment of osteoarthrosis, cartilage damage, tendon damage, ligament damage, or joint disorders which comprises injecting into a subject in need thereof a therapeutically effective amount of a biological material comprising:
   component (a): a liquid carrier comprising a viscous solution containing at least one member selected from the group consisting of natural polysaccharides and semi-synthetic polysaccharides, and having a dynamic viscosity of and between 0.1 and 0.25 Pa·s (100 and 250 cPoise) measured at 20° C. at shear rate of D=350 s$^{-1}$, and/or a Kinematic viscosity comprised between 0.99× 10$^{-4}$ and 2.48×10$^{-4}$ m$^2$/sec (99 and 248 cSt) measured at 20° C. and at shear rate of D=350 s$^{-1}$, and
   component (b): at least one member selected from the group consisting of (i) a culture or an extemporaneous preparation of mesenchymal stem cells, and (ii) a platelet rich hemo-derivative;
   wherein said viscous solution of the component (a) is selected from the group consisting of:
   (I) an aqueous solution of a hyaluronic acid or a pharmaceutically acceptable salt thereof, with average molecular weight of between 450 and 730 kDa in a concentration of 10 mg/ml,
   (I) an aqueous solution of hexadecylamide of hyaluronic acid having an average molecular weight in the range of 450 and 730 kDa, in a concentration of between 0.2 and 1.5 mg/ml.

11. The therapeutic method according to claim 10, wherein said component (a) comprises the aqueous solution (II) wherein the concentration of the hexadecylamide of hyaluronic acid is between 0.5 and 1 mg/ml.

12. The therapeutic method according to claim 10, wherein said component (b) comprises mesenchymal stem cells of the autologous type selected from the group consisting of bone marrow mesenchymal stem cells, peripheral blood mesenchymal stem cells, periosteum mesenchymal stem cells, umbilical cord mesenchymal stem and cells of adipose tissue.

13. The therapeutic method according to claim 10 for the treatment of cartilage damage comprising intra-articularly injecting said biologic material.

14. The therapeutic method according to claim 10, wherein said treatment is for the treatment of Achilles tendon damage.

15. The therapeutic method according to claim 10, wherein said component (b) comprises platelet-rich hemo-derivatives selected from the group consisting of platelet-rich plasma, platelet concentrate, and platelet gel.

* * * * *